United States Patent [19]
Brodie et al.

[11] Patent Number: 5,994,334
[45] Date of Patent: Nov. 30, 1999

[54] ANDROGEN SYNTHESIS INHIBITORS

[75] Inventors: Angela Brodie, Fulton, Md.; Yangzhi Ling, Beijing, China

[73] Assignee: University of Maryland, Baltimore, Md.

[21] Appl. No.: 08/795,932

[22] Filed: Feb. 5, 1997

[51] Int. Cl.⁶ ............................. A61K 31/58; C07J 43/00
[52] U.S. Cl. ............................................. 514/176; 540/96
[58] Field of Search ............................... 540/96; 514/176

[56] References Cited

U.S. PATENT DOCUMENTS

| | | | |
|---|---|---|---|
| 2,664,423 | 12/1953 | Rorig | 260/239.5 |
| 3,313,809 | 4/1967 | Clinton et al. | 260/239.55 |
| 3,317,520 | 5/1967 | Clinton | 260/239.5 |
| 5,264,427 | 11/1993 | Brodie et al. | 514/177 |
| 5,604,213 | 2/1997 | Barrie et al. | 514/176 |

OTHER PUBLICATIONS

Njar et al., "Nucleophilic Vinylic 'Addition–Elimination' Substitution Reaction of 3B–Acetoxy–17–Chloro–16–Formylandrosta–5,16–Diene: A Novel and General Route to 17–Substituted Steroids" *Bioorganic and Medical Chemistry Letters* 6:2777–2782, 1996, No. 22.

Njar et al., Bioorg and Medicinal Chem., vol. 6, No. 22, pp. 2777–2782., 1996.

Rasmusson et al., Annual Reports in Med.Chem. Acad. Press., 1994., Chap 23.

Angelastro, M.R., et al. "17β–(Cyclopropylamino)–Androst–5–En–β–Ikm A Selective Mechanism–Based Inhibitor of Cytochrome P450$_{17\alpha}$ (Steroid 17α–Hydroxylase/C$_{17-20}$ Lyase)" *Biochem. Biophys. Res. Commun.* 162:1571–1577, 1989.

Ayub, M. et al. "Inhibition of Testicular 17α–Hydroxylase and 17,20–Lyase but not 3β–Hydroxysteroid Dehydrogenase–Isomerase or 17β–Hydroxysteroid Oxidoreductase by Ketoconazole and Other Imidazole Drugs" *J. Steroid Biochem.* 28:521–531, 1987.

Banks, P.K., et al. "Regulation of Ovarian Steroid Biosynthesis by Estrogen during Proestrus in the Rat" *Endocrinology* 129: 1295–1304, 1991.

Barrie, S.E. "Inhibition of 17α–Hydroxylase/C17–C20 Lyase by Bifluranol and its Analogues" *J. Steroid Biochem.* 33:1191–1195, 1989.

Brodie, A.M.H. et al., "Studies on the Mechanism of Estrogen Biosynthesis in the Rat Ovary–I" *J. Steroid Biochem.* 7:787–793, 1976.

Brodie, A.M.H. et al., "Inactivation of Aromatase In vitro by 4–Hydroxy–4–Androstene–3, 17–Dione and 4–Acetoxy–4–Androstene–3, 17–Dione and Sustained Effects in vivo" *Steroids*, 38:693–702, 1981.

Brodie, A.M.H., et al. "Lack of Evidence for Aromatase in Human Prostatic Tissues: Effects of 4–Hydroxyandrostenedione and Other Inhibitors on Androgen Metabolism" *Cancer Research*, 49:6551–6555, 1989.

Brodie, A.M.H. "Inhibitors of Steroid Biosynthesis" (Ch. 16) in Design of Enzyme Inhibitors as Drugs, vol. 2, (Eds) M. Sandler and H.J. Smith, Oxford University Press, pp. 503–522, 1993.

Brodie, A.M.H. "Steroidogenesis Pathway Enzymes—Introduction" (Ch. 9) in Design of Enzyme Inhibitors as Drugs vol. 2, (Eds) M. Sandler and H.J. Smith, Oxford University Press, pp. 1–13, 1993.

Brodie, A.M.H. "Steroidogenesis Pathway Enzymes—Aromatase Inhibitors" (Section 9B) in Design of Enzyme Inhibitors as Drugs vol. 2, (Eds) M. Sandler and H.J. Smith, Oxford University Press, pp. 424–438, 1993.

Bruchovsky, N. et al. "The Conversion of Testosterone to 5α–Androstan–17β–ol–3–one by Rat Prostate in Vivo and in Vitro" *J. Biol. Chem.* 243: 2012–2021, 1968.

Bulun et al., "Use of Tissue–Specific Promoters in the Regulation of Aromatase Cytochrome P450 Gene Expression in Human Testicular and Ovarian Sex Cord Tumors, as well as in Normal Fetal and Adult Gonads" *J. Clin. Endocrinol. Metab.* 77:1616–1621, 1993.

Chomczynski, P. et al. "Single–Step Method of RNA Isolation by Acid Guanidinium Thiocyanate–Phenol–Chloroform Extraction" *Anal. Biochem.* 162:156–159, 1987.

Church, G. M. et al. "Genomic Sequencing" *Proc. Soc. Natl. Acad. Sci.* 81:1991–1995, 1984.

Cohen SM, et al. "Comparison of the Effects of New Specific Azasteroid Inhibitors of Steroid 5α–Reductase on Canine Hyperplastic Prostate: Suppression of Prostatic DHT Correlated with Prostate Regression" *The Prostate* 26:55–71, 1995.

Coen, P., et al. "An Aromatase–Producing Sex–Cord Tumor Resulting in Prepubertal Gynecomastia" *New Eng. J. Med.* 324:317–322, 1991.

Coombes R.C. et al. "4–Hydroxy Androstenedione Treatment for Postmenopausal Patients with Advanced Breast Cancer" *Steroids* 50:245–252, 1987.

Covey, D.F. et al., "10β–Propynyl–substituted Steroids" *J. Biol. Chem.*, 256: 1076, 1980.

(List continued on next page.)

*Primary Examiner*—Richard L. Raymond
*Assistant Examiner*—Pavanaram K Sripada
*Attorney, Agent, or Firm*—Burns, Doane, Swecker & Mathis, L.L.P.

[57] ABSTRACT

This invention relates to novel inhibitors of androgen synthesis that are useful in the treatment of prostate cancer and benign prostatic hypertrophy. Novel compounds according to the present invention are steroid derivatives. These compounds are preferably substituted at the 17 position, with a heterocyclic or nonheterocyclic radical, for example, a 5-membered heterocyclic ring. The present invention also provides methods of synthesizing these novel compounds, pharmaceutical compositions containing these novel compounds, and methods of treating prostate cancer and benign prostatic hypertrophy using the androgen synthesis inhibitors of the present invention.

23 Claims, 2 Drawing Sheets

OTHER PUBLICATIONS

Crawford, E.D. et al. "A Controlled Trial of Leuprolide with and without Flutamide in Prostatic Carcinoma" *N. Engl. J. Med.*, 321: 419–424, 1989.

di Salle, E. et al. "Effects of 5α–Reductase Inhibitors on Intraprostatic Androgens in the Rat" *J. Steroid Biochem. Mol. Biol.*, 53, 1–6: 381–385, 1995.

Doorenbos, N.J., et al. "17α–Isoxazolyl and 17β–Pyrazolyl Steroids from 3β–Hydroxy–21–formylpregn–5–en–20–one." *J. Org. Chem.*, 31: 3193, 1996.

Forti, G., et al. "Three–Month Treatment with a Long–Acting Gonadotropin–Releasing Hormone Agonist of Patients with Benign Prostatic Hyperplasia: Effects on Tissue Androgen Concentration, 5α–Reductase Activity and Androgen Receptor Content" *J. Clin. Endocrinol. Metab.* 68:461–468, 1989.

Frye, S. et al. "6–Azasteroids: Potent Dual Inhibitors of Human Type 1 and 2 Steroid 5α–Reductase" *J. Med. Chem.* 36: 4313–4315, 1993.

Gaddipati J.P. et al., "Frequent Detection of Codon 877 Mutation in the Androgen Receptor Gene in Advanced Prostate Cancers" *Cancer Res.* 54: 2861–2864, 1994.

Geller, J. et al., "Comparison of Prostatic Cancer Tissue Dihydrotestosterone Levels at the Time of Relapse Following Orchiectomy or Estrogen Therapy" *J. Urology* 132:693–696, 1984.

Gold, R. et al., "Detection of DNA Fragmentation in Apoptosis: Application of In situ Nick Translation to Cell Culture Systems and Tissue Sections" *J. Histochem. Cytochem.* 41,7:1023–1030, 1993.

Goldman, A.S. et al., "Production of Male Pseudohermaphroditism in Rats by Two New inhibitors of Steroid 17α–Hydroxylase and C17–20 Lyase" *J. Endoc.* 71: 289, 1976.

Gormley, G.J. "Role of 5α–Reductase Inhibitors in the Treatment of Advanced Prostatic Carcinoma" *Urol. Clinics of North America* 18, 1:93–97, 1991.

Goss, P.E. et al. "Treatment of Advanced Postmenopausal Breast Cancer with an Aromatase Inhibitor, 4–Hydroxyandrostenedione: Phase II Report" *Cancer Res.* 46:4223–4826, 1986.

Goya, S. et al., "Studies on Cardiotonic Steroid Analogs" *Yakugaku Zasshi.,* 90: 537, 1970.

Haase–Held, M., et al. "The Synthesis of 4–Cyanoprogesterone: A Potent Inhibitor of the Enzyme 5–α–Reductase" *J. Chem. Soc. Perkin Trans. I*:2999, 1992.

Habenicht, U.F., et al. "Induction of Estrogen–Related Hyperplastic changes in the Prostate of the Cynomolgus Monkey (*Macaca fascicularis*) by Androstenedione and its Antagonization by the Aromatase Inhibitor 1–Methyl–Androsta–1, 4–Diene–3, 17–Dione" *Prostate,* 11:313–326, 1987.

Haffner, "Synthesis of 6–Azacholesten–3–ones: Potent Inhibitors of 5α–Reductase", *Tetrahedron Letters* 36:4039–4042, No. 23, 1995.

Hamilton, G.A. "Chemical Models and Mechanisms of Oxygenases" In *"Molecular Mechanisms of Oxygen Activation"*; Hayishi, O., Ed.; Academic Press: New York: 405, 1974.

Harada, "Novel Properties of Human Placental Aromatase as Cytochrome P–450: Purification and Characterization of a Unique Form of Aromatase", *J. Biochem* 103:106–113 (1988).

Henderson, D. "Estrogens and Benign Prostatic Hyperplasia: Rationale for Therapy with Aromatase Inhibitors" *Annals Med.* 23:201–203, 1991.

Hoehn, W., et al. "Human Prostatic Adenocarcinoma: Some Characteristics of a Serially Transplantable Line in Nude Mice (PC82)" *Prostate* 1:94–104, 1980.

Holt, D.A., et al. "Inhibition of Steroid 5α–Reductase by Unsaturated 3–Carboxysteroids" *J. Med. Chem.* 33: 943–950, 1990.

Hsiang, Y.H.H. et al. "The Influence of 4–Hydroxy–4–Androstene–3, 17–Dione on Androgen Metabolism and Action in Cultured Human Foreskin Fibroblasts" *J. Steroid Biochem.* 26:131–136, 1987.

Huynh, C. et al. "Fixation d'un Groupe Nitrile en Position 4 des Céto–3$\Delta^4$–stéroides" *Bull. Soc. Chim. Fr.*: 4396, 1971.

Inkster et al., "Human Testicular Aromatase: Immunocytochemical and Biochemical Studies" *J. Clin. Endocrinol. Metab.* 80:1941–1947, 1995.

Ishibashi, K. et al. "Synthesis of B–NOR–4–AZA–5α–Androstane Compounds as 5α–Reductase Inhibitor" *Bioorg. & Med. Lett.,* 4: 729–732, 1994.

Jarman, M., et al. "Hydroxyperfluoroazobenzenes: Novel Inhibitors of Enzymes of Androgen Biosynthesis" *J. Med. Chem.* 33:2452–2455, 1990.

Kitz, R. et al., "Esters of Methanesulfonic Acid as Irreversible Inhibitors of Acetylcholinesterase" *J. Biol. Chem.* 237: 3245–3249, 1962.

Klus, G. et al. "Growth Inhibition of Human Prostate Cells in Vitro by Novel Inhibitors of Androgen Synthesis" *5th Int'l Cong. on Hormones & Cancer,* Abst. 83, 1995.

Kozak, I., et al. "Nuclei of Stroma: Site of Highest Estrogen Concentration in Human Benign Prostatic Hyperplasia" *Prostate* 3:433–438, 1982.

Krieg, M., et al. "Stroma of Human Benign Prostatic Hyperplasia: Preferential Tissue for Androgen Metabolism and Oestrogen Binding" *Acta Endocri. (Copehn.)* 96:422–432, 1981.

Kyprianou, N., et al. "Programmed Cell Death During Regression of PC–82 Human Prostate Cancer following Androgen Ablation" *Cancer Research* 50:3748–3753, 1990.

Kyprianou, N. et al. "Expression of Transforming Growth Factor–β in the Rat Ventral Prostate during Castration–Induced Programmed Cell Death" *Mol. Endocrin.* 3:1515–1522, 1989.

Labrie, F. et al. "Combination Therapy for Prostate Cancer" *Cancer Suppl.* 71:1059–1067, 1993.

Li J., et al. "4–Pregnene–3–One–20β–Carboxaldehyde: A Potent Inhibitor of 17α–Hydroxylase/$C_{17,20}$ –Lyase and of 5α–Reductase" *J Steroid Biochem. Mol. Biol.* 42:313–321, 1992.

Li, J. et al. "Inhibition of Androgen Synthesis by 22–Hydroximino–23,24–Bisnor–4–Cholen–3–One" *The Prostate,* 26:140–150, 1995.

Li, J. et al. "Synthesis and evaluation of pregnane derivatives as inhibitors of human testicular 17α–hydroxylase/$C_{17,20}$–lyase" *J. Med. Chem.* 39:4335–4339, 1996.

Lu Q., et al. "Expression of Aromatase Protein and Messenger Ribonucleic Acid in Tumor Epithelial Cells and Evidence of Functional Significance of Locally Produced Estrogen in Human Breast Cancers" *Endocrinology* 137:3061–3068, No. 7, 1996.

Mawhinney, M.G. et al. "Androgens and Estrogens in Prostatic Neoplasia" *Adv. Sex Horm Res* 2:41–209, 1976.

McCague, R. et al. "Inhibition of Enzymes of Estrogen and Androgen Biosynthesis by Esters of 4–Pyridylacetic Acid" *J. Med. Chem.* 33:3050–3055, 1990.

McDonald, I.A., et al. "Inhibition of Steroid 5α–Reductase by 'Inverted,' Competitive Inhibitors" *Bioorg. & Med. Lett.* 4: 847–851, 1994.

Metcalf, B.W., et al. "Substrate–Induced Inactivation of Aromatase by Allenic and Acetylenic Steroids" *J. Am. Chem. Soc.* 103: 3221, 1981.

Nakajin, S. et al. "Microsomal Cytochrome P–450 from Neonatal Pig Testis" *J. Biol. Chem.* 256:3871–3876, 1981.

Nakajin, S., et al. "Microsomal Cytochrome P–450 from Neonatal Pig Testis: Two Enzymatic Activities (17α–Hydroxylase and $C_{17,20}$–Lyase) Associated with One Protein" *Biochem.* 20:4037–4042, 1981.

Nakajin, S. et al. "Inhibitory Effects and Spectral Changes on Pig Testicular Cytochrome P–450(17α–Hydroxylase/Lyase) by 20α–Hydrox–$C_{21}$–Steroids" *Yakugaku Zasshi.* (Japan), 108:1188–1195, 1988.

Njar, V.C.O., et al. "Novel 10α–Aziridinyl Steroids; Inhibitors of Aromatase" *J. Chem. Soc. Perkin Trans* 1: 1161, 1993.

Onoda, M. et al. "Affinity Alkylation of the Active Site of $C_{21}$ Steroid Side–Chain Cleavage Cytochrome P–450 from Neonatal Porcine Testis: A Unique Cysteine Residue Alkylated by 17–(Bromoacetoxy) progesterone" *Biochemistry,* 26: 657, 1987.

Pataki, J., et al. "Synthesis of Fluorinated 3β–Hydroxypregn–5–EN–20–One Derivatives" *Steroid,* 28: 437–447, 1976.

Pelc, B., et al. "Androstane Derivatives Substituted by Pyrazole Ring in Position 17" *Collection Czechoslov, Chem. Commun.,* 34: 442, 1969.

Petrow, V., et al. "Studies on a 5α–Reductase Inhibitor and Their Therapeutic Implications" The Prostatic cell: *Structure and Function Part B*: 283–297, 1981, Alan R. Liss Inc., 150 Fifth Avenue, New York, NY 10011.

Potter G.A., et al. "Novel Steroidal inhibitors of Human Cytochrome $P450_{17\alpha}$ (17α–Hydroxylase–$C_{17,20}$O–lyase): Potential Agents for the Treatment of Prostatic Cancer" *J. Med. Chem.* 38: 2463–2471, 1995.

Rasmusson, G.H., et al. "Azasteroids: Structure–Activity Relationships for Inhibition of 5α–Reductase and of Androgen Receptor Binding" *J. Med. Chem.* 29:2298–2315, 1986.

Rasmusson, G.H., et al. "Azasteroids as Inhibitors of Rat Prostatic 5α–Reductase" *J. Med. Chem.* 27: 16901701, 1984.

Rittmaster, R.S., et al. "Differential Effect of 5α–Reductase Inhibition and Castration on Androgen–Regulated Gene Expression in Rat Prostate" *Mol Endocrin.* 5:1023–1029, 1991.

Russell, D.W., et al. "Steroid 5α–Reductase: Two Genes/Two Enzymes" *Ann. Rev. Biochem.* 63:25–61, 1994.

Schieweck, K., et al. "Anti–Tumor and Endocrine Effects of Non–Steroidal Aromatase Inhibitors on Estrogen–Dependent Rat Mammary Tumors" *J. Steroid Biochem. Mol. Biol.* 44: 633–636, 1993.

Schwarzel, W.C., et al. "Studies on the Mechanism of Estrogen Biosynthesis. VIII. The Development of Inhibitors of the Enzyme System in Human Placenta" *Endocrinology* 92:866–880, 1973.

Shao, T. C., et al. "Effects of Finasteride on the Rat Ventral Prostate" *J. Androl.* 14:79–86, 1993.

Shearer, R. et al. "Studies in Prostatic Cancer with 4–Hydroxyandrostenedione" In: Coombes, R.C. and Dowsett, M. (eds.), 4–hydroxyandrostenedione—A new approach to hormone–dependent cancer. pp. 41–44, 1991.

Sjoerdsma, A. "Suicide Enzyme Inhibitors as Potential Drugs" *Clin. Pharmacol. Ther.* 30:3, 1981.

Snider, C.E., et al. "Covalent Modification of Aromatase by a Radiolabeled Irreversible Inhibitors" *J. Steroid Biochem.* 22: 325, 1985.

Stoner, E. "The Clinical Development of a 5r–Reductase Inhibitor, Finasteride" *J. Steroid Biochem. Molec. Biol.* 37:375–378, 1990.

Trachtenberg, J. "Ketoconazole Therapy in Advanced Prostatic Cancer" *J. Urol.* 132:61–63, 1984.

Van Steenbrugge, G.J., et al. "Transplantable Human Prostatic Carcinoma (PC–82) in Athymic Nude Mice III. Effects of Estrogens on the Growth of the Tumor Tissue" *Prostate* 12:157–171, 1988.

Veldscholte, J., et al. "Anti–Androgens and the Mutated Androgen Receptor of LNCaP Cells; Differential Effects on Binding Affinity, Heat–Shock Protein Interaction, and Transcription Activation" *Biochemistry* 31:2393–2399, 1992.

Vescio R.A., et al. "Cancer Biology for Individualized Therapy: Correlation of Growth Fraction Index in Native–State Histoculture with Tumor Grade and Stage" *Proc Natl Acad Sci USA* 87: 691–695, 1990.

Visakorpi, T., et al. "In vivo Amplification of the Androgen Receptor Gene and Progression of Human Prostate Cancer" *Nature Genetics* 9: 401–406, 1995.

Wainstein M.A., et al. "CWR22: Androgen–dependent Xenograft Model Derived from a Primary Human Prostatic Carcinoma" *Cancer Res.* 54:6049–6052, 1994.

Weintraub, P.M., et al. *Merrel Dow Pharmaceuticals Inc.,* EP O: 469–548 A2, 1991. (Abstract).

Weintraub, P.M., et al. *Merrel Dow Pharmaceuticals Inc.,* CA 116: 214776v, 1992. (Abstract).

Weintraub, P.M., et al. *Merrel Dow Pharmaceuticals Inc.,* EP O: 469–547 A2, 1991. (Abstract).

Williams, G., et al. "Objective Responses to Ketoconazole Therapy in Patients with Relapsed Progressive Prostatic Cancer" *Br. J. Urol.* 58: 45–51, 1986.

Yue, W., et al. "A New Nude Mouse Model for Postmenopausal Breast Cancer Using MCF–7 Cells Transfected with the Human Aromatase Gene" *Cancer Res.* 54:5092–5095, 1994.

Yue, W., et al. "Effect of Aromatase Inhibitors on Growth of Mammary Tumors in a Nude Mouse Model" *Cancer Res.* 55: 3073–3077, 1995.

Zhou, J.L., et al. "The Effect of Aromatase Inhibitor 4–Hydroxyandrostenedione on Steroid Receptors in Hormone–Dependent Tissues of the Rat" *J. Steroid Biochem. Mol. Biol.* 52:71–76, 1995.

Yang–zhi Ling et al, (1997), "17–Imidazolyl, pyrazolyl, and isoxazolyl androstene derivatives. Novel steroidal inhibitors of human cytochrome C17,20–lyase (P45017α)", J. Med. Chem. 40:3297–3304.

V.C.O. Njar et al, (1999), "Inhibitors of 17α–hydroxylase/17,20–lyase (CYP17): Potential agents for the treatment of prostate cancer", Current Pharmaceutical Design, 5:163–180.

Brian J. Long et al, (1999), "Effects of novel inhibitors of androgen synthesis on the growth of human prostate cancer in vitro and in vivo", (manuscript).

Dmitry N. Grigoryev et al, (1999), "Cytochrome P450c17–expressing *Escherichia coli* as a fist–step screening system for 17α–hydroxylase–C17,20–lyase inhibitors", Anal. Biochem., 267:319–330.

ANDROGEN SYNTHESIS INHIBITORS

BACKGROUND OF THE INVENTION

1. Field of the Invention

This invention relates to novel inhibitors of androgen synthesis that are useful in the treatment of prostate cancer and benign prostatic hypertrophy. The present invention also provides methods of synthesizing these novel compounds, pharmaceutical compositions containing these novel compounds, and methods of treating prostate cancer and benign prostatic hypertrophy using the androgen synthesis inhibitors of the present invention.

2. Description of the Related Art

Prostate cancer now ranks as the most prevalent cancer in men. Approximately 160,000 new cases are diagnosed each year; of these, 35,000 will die of metastatic disease. In women, breast cancer kills 45,000 women per year. The present inventors have previously proposed that selective aromatase (estrogen synthetase) inhibitors to control estrogen production would be potentially useful agents for breast cancer. In men, aromatase inhibitors may be useful for conditions associated with estrogen excess, such as gynecomastia and oligospermia (Coen et al., 1991; Hsiang et al., 1987). It has been suggested that aromatase inhibitors might also be of value in prostatic cancer and benign prostatic hypertrophy (BPH) (Henderson et al., 1991).

In 1973, the present inventors reported the first of a number of compounds which are potent and selective inhibitors of aromatase (Schwarzel et al., 1973). The most active of those inhibitors, 4-hydroxyandrostene-3,17-dione (4-OHA) (Brodie et al., 1976), was found to act by rapid competitive inhibition followed by inactivation of the enzyme in vitro which appeared to be long-lasting or irreversible (Brodie et al. 1981). Enzyme inhibitors with these properties are thought to bind to the active site of the enzyme, are likely to be quite specific and should have long-lasting effects in vivo due to inactivation of the enzyme (Sjoerdsma, 1981). The present inventors further demonstrated that 4-OHA reduces peripheral plasma estrogen levels and causes significant regression of breast cancers in postmenopausal patients with advanced metastatic disease who have relapsed from other hormonal treatment, such as ovariectomy and tamoxifen. The compound has both oral and parenteral activity and is without significant side effects in these patients (Goss et al., 1986; Coombes et al. 1987). 4-OH-A (formastane) is now approved for treatment of breast cancer in many countries worldwide, including most European countries and Canada since 1995. It is the first new treatment for breast cancer in 10 years.

In men, estrogens are produced by the testes and by peripheral aromatization of adrenal androgens. Testosterone is the major product of the testis and is converted by 5α-reductase to the more potent androgen, dihydrotestosterone (DHT), in the prostate (Bruchovsky et al., 1968). While androgens are of primary importance in the growth of normal prostate, benign prostatic hypertrophy (BPH) and prostatic cancer, several lines of evidence suggest that estrogens also may have a role (Mawhinney et al, 1976).

4-OHA also inhibits 5α-reductase in vitro, although with less potency than it inhibits aromatase (Brodie et al. 1989b). Because of these two activities, the possibility that 4-OHA might be effective in prostatic cancer was explored in a small group of men with advanced disease. Subjective responses were observed in 80% of these patients, although there was no clear evidence of objective remissions (Shearer et al., 1991). Estrogen levels were reduced as expected but DHT concentrations were unchanged in the patients. The latter finding in addition to the weak androgenic activity of the compound may have determined the lack of objective responses.

Chemotherapy is usually not highly effective and is not a practical option for most patients with prostatic cancer because of the adverse side-effects which are particularly detrimental in older patients. However, the majority of patients initially respond to hormone ablative therapy although they eventually relapse, as is typical with all cancer treatments. Current treatment by orchidectomy or administration of gonadotropin-releasing hormone (GnRH) agonists result in reduced androgen production by the testis but does not interfere with androgen synthesis by the adrenals. Following 3 months of treatment with a GnRH agonist, testosterone and DHT concentrations in the prostate remained at 25% and 10%, respectively, of pretreatment levels (Foti et al., 1989). Similarly, about 20% of castrated patients in relapse had significant levels of DHT in their prostatic tissue (Geller et al., 1984). These finding suggest that the adrenals contribute precursor androgens to the prostate. This is supported by clinical studies of patients receiving combined treatment with either GnRH or orchidectomy and an antiandrogen, such as flutamide, to block the actions of androgens, including adrenal androgens. Such patients have increased progression-free survival time compared to patients treated with GNRH agonist or orchidectomy alone (Crawford et al., 1989; Labrie et al., 1993).

Although patients initially respond to endocrine therapy, they frequently relapse. It was reported recently that in 30% of recurring tumors of patients treated with endocrine therapy, high-level androgen receptor (AR) amplification was found (Visakorpi et al., 1995). Also, flutamide tended to interact with those mutant AR and stimulate prostatic cell growth. This suggests that AR amplification may facilitate tumor cell growth in low androgen concentrations. Thus, total androgen blockade as first line therapy may be more effective than conventional androgen deprivation by achieving maximum suppression of androgen concentrations which may also prevent AR amplification (Kellens, 1993). It is presently unclear whether sequential treatment with different agents can prolong the benefits of the initial therapy. New agents which act by different mechanisms could produce second responses in a portion of relapsed patients. Although the percentage of patients who respond to second-line hormonal therapy may be relatively low, a substantial number of patients may benefit because of the high incidence of prostatic cancer. Furthermore, there is the potential for developing more potent agents than current therapies, none of which are completely effective in blocking androgen effects.

The 17α-hydroxylase/$C_{17,20}$-lyase is a key enzyme in the biosynthesis of androgens and converts the $C_{21}$ steroids (pregnenolone and progesterone) to the $C_{19}$ androgens, dehydroepiandrosterone (DHEA), 5-androstenediol (A-diol), testosterone, and androstenedione in the testis and adrenals. Some inhibitors of 17α-hydroxylase/$C_{17,20}$-lyase have been described (Barrie et al., 1989; McCague et al., 1990; Jarman et al., 1990; Ayub et al., 1987; Nakajin et al., 1988, 1989; Angelastro et al., 1989; Potter et al., 1995). Ketoconazole, an active imidazole fungicide, is the only inhibitor used currently to reduce testosterone biosynthesis in the treatment of patients with advanced prostatic cancer (Trachtenberg et al., 1984; Willimas et al., 1986). However, ketoconazole is not very potent. Moreover, it has a number of significant side-effects, including inhibition of several other cytochrome $P_{450}$ steroidogenic enzymes, and reduction of cortisol production. Another drug used for prostate cancer, aminoglutethimide (AG), has similar drawbacks. This suggest that more potent and selective inhibitors of this enzyme could provide useful agents in treating this disease. In addition such compounds may be effective in treating breast cancer patients. AG was used for this purpose, but was associated with adverse side-effects.

In the prostate, 5α-reductase is the enzyme that converts testosterone to the more potent androgen, DHT, which stimulates prostatic growth. This enzyme occurs in two important isoforms, the Type I isoform expressed in human non-genital skin, and the Type II isoform present in the human prostate (see, Russell et al., 1994). The 5α-reductase inhibitor, N-[1,1-dimethyl-3-oxo-4-aza-5αandrost-1-ene-17β-carboxamide (finasteride; Merck) recently approved for treatment of BPH (Stoner, 1990) is a more potent inhibitor of the Type II than of the Type I isoform. However, finasteride is effective mainly in BPH patients with minimal disease, possibly because serum DHT levels have been found to be incompletely reduced (65–80%). As the Type I isoenzyme is probably the source of much of the residual plasma DHT, compounds that inhibit Type I as well as Type II may be more effective in patients. More recently, another azasteroid MK-434 has been described which reduces prostatic DHT levels in dogs more effectively than finasteride (Cohen et al., 1995). The main advantage of this compound, which has similar activity to finasteride in vitro, appears to be its more favorable pharmacokinetics. However, its efficacy in humans remains to be seen. Although these compounds reduce DHT levels, they also increase serum testosterone levels. Preservation of testosterone levels may be an advantage in patients with BPH. However, inhibitors of 5α-reductase which increase testosterone levels may not be sufficiently effective in treating prostatic cancer. While DHT binds to the androgen receptor with higher affinity than testosterone and dissociates more slowly, testosterone can bind to the receptor when DHT levels are reduced (Gormley, 1991). As indicated above, despite significant reductions in prostatic DHT levels during treatment (Cohen et al, 1995), these compounds are not as effective as castration. More importantly, it appears that they are less effective in eliciting prostatic cell death. The androgen-responsive gene, TRPM-2 associated with apoptosis is significantly enhanced by castration but not by finasteride treatment (Rittermaster et al., 1991; Shao et al, 1993). This has been attributed to the lower androgen levels after castration (Shao et al., 1993), which is mainly a consequence of the reduction in testosterone production. Recent studies of patients receiving long-term treatment with finasteride found some patients developed gynecomastia which led to breast cancer in a few cases (NEJM, Sept., 1996, letter to the editor). This raises concers about the use of 5α-reductase inhibitors since blockade of this step increases the conversion of androgen substrates to estrogens. Compounds which reduce production of testosterone and DHT as well as other androgens by inhibiting 17-hydroxylase/lyase would not be associated with this problem and may be more effective in treatment of prostatic cancer.

REFERENCES

The following references are representative of the state of the art with respect to steroid compounds and their use in the treatment of BPH and prostate cancer.

Angelastro, M. R., et al. *Biochem. Biophys. Res. Commun.* 162:1571–1577, 1989.
Ayub, M. et al. *J. Steroid Biochem.* 28:521–531, 1987.
Banks, P. K., et al. *Endocrinology* 129: 1295–1304, 1991.
Barrie, S. E. *J. Steroid Biochem.* 33:1191–1195, 1989.
Brodie, A. M. H. et al., *J. Steroid Biochem.* 7:787–793, 1976.
Brodie, A. M. H. et al., *Steroids,* 38:693–702, 1981.
Brodie, A. M. H., et al. *Cancer Research,* 49:6551–6555, 1989b.
Brodie, A. M. H. et al. U.S. Pat. No. 5,264,427
Brodie, A. M. H. Steroidogenic Inhibitors—Introduction in Design of Enzyme Inhibitors as Drugs Vol. 2, (Eds) M. Sandler and H. J. Smith, Oxford University Press, 1993a.
Brodie, A. M. H. Aromatase in Design of Enzyme Inhibitors as Drugs Vol. 2, (Eds) M. Sandler and H.J. Smith, Oxford University Press, 1993b.
Bruchovsky, N. et al. *J. Biol. Chem.* 243: 2012–2021, 1968.
Bulun et al., *J. Clin. Endocrinol. Metab.* 77:1616–1621, 1993
Chomczynski, P. et al. *Anal. Biochem.* 162:156–159, 1987.
Church, G. M. et al. *Proc. Soc. Natl. Acad. Sci.* 81:1991–1995, 1984.
Cohen SM, et al. *The Prostate* 26:55–71, 1995.
Coen, P., et al. *New Eng. J. Med.* 324:317–322, 1991.
Coombes R. C. et al. *Steroids* 50:245–252, 1987.
Covey, D. F. et al., *J. Biol. Chem.,* 256: 1076, 1980.
Crawford, E. D. et al. *N. Engl. J. Med.,* 321: 419–424, 1989.
di Salle, E. et al. *J. Steroid Biochem. Mol. Biol.,* 53, 1–6: 381–385, 19§5.
Doorenbos, N. J., et al. *J. Org. Chem.,* 31: 3193, 1966.
Forti, G., et al. *J. Clin. Endocrinol. Metab.* 68:461–468, 1989.
Frye, S. et al. *J. Med. Chem.* 36: 4313–4315, 1993.
Gaddipati J. P. et al., *Cancer Res.* 54: 2861–2864, 1994.
Geller, J. et al., *J. Urology* 132:693–696, 1984.
Gold, R. et al., *J. Histochem. Cytochem.* 41,7:1023–1030, 1993.
Goldman, A. S. et al., *J. Endoc.* 71: 289, 1976.
Gormley, G. J. *Urol. Clinics of North America* 18, 1: 93–97, 1991.
Goss, P. E. et al. *Cancer Res.* 46:4223–4826, 1986.
Goya, S. et al., *Yakugaku Zasshi.,* 90: 537, 1970.
Haase-Held, M., et al. *J. Chem. Soc. Perkin Trans.* 1:2999, 1992.
Habenicht, U. F., et al. *Prostate,* 11:313–326, 1987.
Hamilton, G. A. In *"Molecular Mechanisms of Oxygen Activation";* Hayishi, O., Ed.; Academic Press: New York: 405, 1974.
Henderson, D. *Annals Med.* 23:201–203, 1991.
Hoehn, W., et al. *Prostate* 1:94–104, 1980.
Holt, D. A., et al. *J. Med. Chem.* 33: 943–950, 1990.
Hsiang, Y. H. H. et al. *J. Steroid Biochem.* 26:131–136, 1987.
Huynh, C. et al. *Bull. Soc. Chim. Fr.:* 4396, 1971.
Inkster et al., *J. Clin. Endocrinol. Metab.* 80:1941–1947, 1995.
Ishibashi, K. et al. *Bioorg. & Med. Lett.,* 4: 729–732, 1994.
Jarman, M., et al. *J. Med. Chem.* 33:2452–2455, 1990.
Kitz, R. et al., *J. Biol. Chem.* 237: 3245–3249, 1962.
Klus, G. et al. *5th Int'l Cong. on Hormones & Cancer,* Abst. 83, 1995
Kozak, I., et al. *Prostate* 3:433–438, 1982.
Krieg, M., et al. *Acta Endocri. (Copenh.)* 96:422–432, 1981.
Kyprianou, N., et al. *Cancer Research* 50:3748–3753, 1990.
Kyprianou, N. et al. *Mol. Endocrin.* 3:1515–1522, 1989.
Labrie, F. et al. *Cancer Suppl.* 71:1059–1067, 1993.
Li J., et al. *J Steroid Biochem. Mol. Biol.* 42:313–321, 1992.
Li, J. et al. *The Prostate,* 26:140–150, 1995
Li, J. et al. Synthesis and evaluation of pregnane derivatives as inhibitors of human testicular 17α-hydroxylase/$C_{17,20}$-lyase. *J. Med. Chem.* in press, 1996

Lu. Q., et al. submitted.
Maloney, P. R. et al. *Tetrahedron Lett.* 36: 4039–4042, 1995.
Maniatis. T., et al. Cold Spring Harbor Laboratory Press, Cold Spring Harbor, N.Y., 1982.
Mawhinney, M. G. et al. *Adv. Sex Horm Res* 2:41–209, 1976.
McCague, R. et al. *J. Med. Chem.* 33:3050–3055, 1990.
McDonald, I. A., et al. *Bioorg. & Med. Lett.* 4: 847–851, 1994.
Metcalf, B. W., et al. *J. Am. Chem. Soc.* 103: 3221, 1981.
Muscato, J. J., et al. *Proc. Am. Assoc. Cancer Res.* 13:22, 1994.
Nakajin, S. et al. *J. Biol. Chem.* 256:3871–3876, 1981a.
Nakajin, S., et al. *Biochem.* 20:4037–4042, 1981b.
Nakajin, S. et al. *Yakugaku Zasshi.* (Japan), 108:1188–1195, 1988.
Njar, V. C. O., et al. *J. Chem. Soc. Perkin Trans* 1: 1161, 1993.
Onoda, M. et al. *Biochemistry*, 26: 657, 1987.
Pataki, J., et al. *Steroid*, 28: 437–447, 1976.
Pelc, B., et al. *Colletion Czechoslov, Chem. Commun.*, 34: 442, 1969.
Petrow, V., et al. *The Prostatic cell: Structure and Function Part B:* 283–297, 1981, Alan R. Liss Inc., 150 Fifth Avenue, New York, N.Y. 10011.
Potter G. A., et al. *J. Med. Chem.* 38: 2463–2471, 1995.
Rasmusson, G. H., et al. *J. Med. Chem.* 29:2298–2315, 1986.
Rasmusson, G. H., et al. *J. Med. Chem.* 27: 16901701, 1984.
Rittinaster, R. S., et al. *Mol Endocrin.* 5:1023–1029, 1991.
Russell, D. W., et al. *Ann. Rev. Biochem.* 63:25–61, 1994.
Schieweck, K., et al. *J. Steroid Biochem. Mol. Biol.* 44: 633–636, 1993.
Schwarzel, W. C., et al. *Endocrinology* 92:866–880, 1973.
Shao, T. C., et al. *J. Androl.* 14:79–86, 1993.
Shearer, R. et al. In: Coombes, R. C. and Dowsett, M. (eds.), 4-hydroxyandrostenedione—A new approach to hormone-dependent cancer. pp. 41–44, 1991.
Sjoerdsma, A. *Clin. Pharmacol. Ther.* 30:3, 1981.
Snider, C. E., et al. *J. Steroid Biochem.* 22: 325, 1985.
Stoner, E. J. *Steroid Biochem. Molec. Biol.* 37:375–378, 1990.
Trachtenberg, J. *J. Urol.* 132:61–63, 1984.
Van Steenbrugge, G. J., et al. *Prostate* 12:157–171, 1988.
Veldscholte, J., et al. *Biochemistry* 31:2393–2399, 1992.
Vescio R. A., et al. *Proc Natl Acad Sci U.S.A.* 87: 691–695.
Visakorpi, T., et al. *Nature Genetics* 9: 401–406, 1995.
Wainstein M. A., et al. *Cancer Res.* 54:6049–6052, 1994.
Weintraub, P. M., et al. *Merrel Dow Pharmaceuticals Inc.*, EP 0: 469–548 A2, 1991.
Weintraub, P. M., et al. *Merrel Dow Pharmaceuticals Inc.*, CA 116: 214776v, 1992.
Williams, G., et al. *Br. J. Urol.* 58: 45–51, 1986.
Yue, W., et al. *Cancer Res.* 54:5092–5095, 1994.
Yue, W., et al. *Cancer Res.* 55: 3073–3077, 1995.
Zhou, J. L., et al. *J. Steroid Biochem. Mol. Biol.* 52:71–76, 1995.

The disclosure of the above publications, patents and patent applications are herein incorporated by reference, as illustrative of the current knowledge of one skilled in the art, in their entirety to the same extent as if the language of each individual publication, patent and patent application were specifically and individually included herein.

Therefore, in view of the aforementioned deficiencies attendant with prior art androgen synthesis inhibitors, including their relative ineffectiveness and their accompanying side effects, it should be apparent that there still exists a need in the art for new types of enzyme inhibitors which potently inhibit 17α-hydroxylase/$C_{17,20}$-lyase as well as 5α-reductase, to block all androgen synthesis could be of benefit in the treatment of prostatic cancer and benign prostatic hypertrophy.

SUMMARY OF THE INVENTION

Accordingly, a major object of the present invention is to provide novel inhibitors of androgen biosynthesis to provide more adequate treatment for patients with prostatic cancer and benign prostatic hypertrophy.

Briefly, the present invention provides novel compounds which reduce testosterone and DHT levels by inhibiting both 17α-hydroxylase/$C_{17,20}$-lyase and 5α-reductase. These compounds provide blockade of all androgen synthesis (androstenedione, testosterone, DHEA and its estrogenic metabolites, as well as DHT) and thus provide more effective treatment of prostate cancer. A number of these compounds are potent inhibitors of 17α-hydroxylase/$C_{17,20}$-lyase and 5α-reductase, and also have antiandrogen activity. Several are much more potent than ketoconazole and almost as potent as finasteride in vitro. Because of their dual activities, these compound could be more effective than current agents in the treatment of prostate cancer. Other compounds that are moderate inhibitors of 17α-hydroxylase/$C_{17,20}$-lyase but are more potent for 5α-reductase may be useful in maintaining a "normal" balance of testosterone and estrogen levels in BPH patients. These compounds are the subject of U.S. Pat. No. 5,264,427, the contents of which are incorporated herein by reference.

A further object of the present invention is to provide pharmaceutical compositions comprising one or more of the 17α-hydroxylase/$C_{17,20}$-lyase and 5α-reductase inhibitors of the present invention, and a pharmaceutically acceptable carrier therefor. These pharmaceutical compositions may be used in the treatment of conditions that require the reduction of testosterone and DHT levels, such as prostate cancer and benign prostatic hypertrophy.

A still further object of the present invention is to provide a method of reducing testosterone and/or DHT levels in a mammalian patient in need of such treatment comprising administering one or more of the 17α-hydroxylase/$C_{17,20}$-lyase and 5α-reductase inhibitors of the present invention in an amount sufficient to reduce testosterone and/or DHT levels by a desired amount.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE PREFERRED EMBODIMENTS OF THE INVENTION

Figure 1:
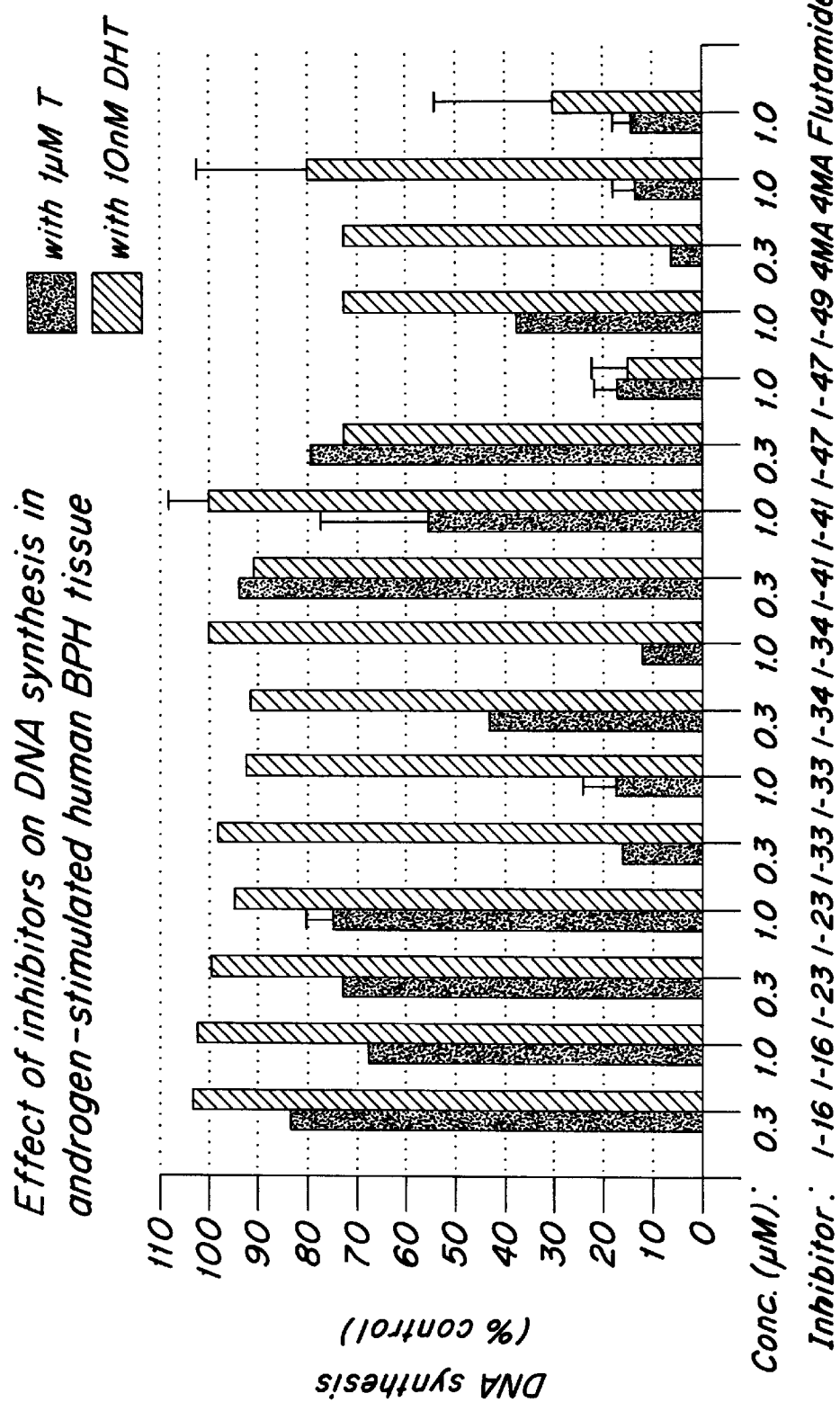
FIG. 1 illustrates the effect of androgen synthesis inhibitors of the present invention on DNA synthesis in androgen-stimulated BPH tissue in culture

This invention arose from a desire of the inventors to improve on previously available compounds used in inhibiting the synthesis of testosterone and DHT. The inventors also sought to provide a safe, effective treatment for BPH and prostate cancer. The inventors have found that administration of the compounds of the present invention effectively blocks synthesis of testosterone and DHT in mammals. Preferred compounds for use in the present invention include compounds of the general formula:

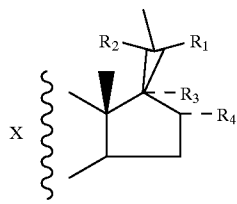

where X represents the residue of the A, B, and C rings of a steroid; $R_3$, $R_4$ represent a hydrogen atom or together represents a double bond; $R_1$ and $R_2$ represent together an oxime, or oxime acetate. A steroid compound according to the present invention preferably further comprises a basic structure selected from the group consisting of 4-en-3-one, 5-en-3β-ol, and 3,5-diene-3-carboxylic acid. Alternatively, a steroid compound according to the present invention may be an azasteroid comprising a ring nitrogen atom in place of a ring carbon atom. Preferably, such an azasteroid will comprise a ring nitrogen in the A ring or the B ring. An azasteroid according to the present invention comprising a ring nitrogen in the A ring will preferably be a 4-azasteroid. An azasteroid according to the present invention comprising a ring nitrogen in the B ring will preferably be a 6-azasteroid. Most preferably, such compounds will be selected from the group consisting of 20β-hydroxy-pregna-4,16-dien-3-one, 16-dehydropregnenolone-20-oxime, 16-dehydroprogesterone, 16-dehydroprogesterone-20-oxime, and acetates thereof.

The present invention also provides compounds of the general formula

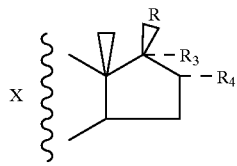

where X represents the residue of the A, B, and C rings of a steroid; R represents a 5-member heterocyclic ring, and $R_3$ and $R_4$ represent a hydrogen atom or together represents a double bond. R is preferably selected from the group consisting of

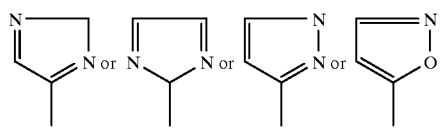

Such steroid compounds according to the present invention preferably further comprise a basic structure selected from the group consisting of 4-en-3-one, 5-en-3β-ol, and 3,5-diene-3-carboxylic acid. Preferably, such a steroid compound is an azasteroid comprising a ring nitrogen atom in place of a ring carbon atom. Preferably, such an azasteroid will comprise a ring nitrogen in the A ring or the B ring. An azasteroid according to the present invention comprising a ring nitrogen in the A ring will preferably be a 4-azasteroid. An azasteroid according to the present invention comprising a ring nitrogen in the B ring will preferably be a 6-azasteroid. Most preferably, such compounds will be selected from the group consisting of 17β-(4'-imidazolyl)-androst-5-en-3β-ol, 17β-(4'-imidazolyl)-androsta-5,16-dien-3β-ol, 17β-(2'-imidazolyl)-androst-5,16-dien-3β-ol, 17β-(3'-pyrzolyl)-androst-5-en-3β-ol, 17β-(3'-pyrazolyl)-androsta-5,16-dien-3β-ol, 17β-(5'-isoxazolyl)-androsta-5,16-dien-3β-ol, and 3-acetates thereof. Alternatively, such compounds are selected from the group consisting of 17β-(4'-imidazolyl)-androst-4-en-3-one, 17β-(4'-imidazolyl)-androsta-4,16-dien-3-one, 17β-(3'-pyrzolyl)-androst-4-en-3-one, 17β14 -(3'-pyrazolyl)-androsta-4,16-dien-3-one, and 17β-(5'-isoxazolyl)-androsta-4,16-dien-3-one.

Pharmaceutical salts of the steroid compounds of the present invention suitable for administration by a variety of routes are known in the art and need not be described herein in detail. Examples of pharmaceutically acceptable salts of the compounds and derivatives thereof according to the invention, include base salts, e.g., derived from an appropriate base, such as alkali metal (e.g., sodium), alkaline earth metal (e.g., magnesium), ammonium, and $HW_nH_m$ bases and salts wherein each of n and m are 0 to 4 and n+m is 4, and wherein W is a $(C_1-C_{18})$alkyl. Pharmaceutically acceptable salts of an acid group or an amino group include, but are not limited to, salts of organic carboxylic acids such as acetic, lactic, tartaric, malic, isothionic, lactobionic and succinic acids; organic sulfonic acids such as methanesulfonic, ethanesulfonic, benzenesulfonic and p-tolylsulfonic acids, and inorganic acids such as hydrochloric, sulfuric, phosphoric and sulfamic acids. Pharmaceutically-acceptable salts of a compound with a hydroxy group include, but are not limited to, the anion of the compound in combination with a suitable cation such as $Na^+$, and $HW_nH_m$, wherein W is a $(C_1-C_{18})$alkyl group, and n and m are 0 to 4, and n+m is 4.

A still further part of this invention is a pharmaceutical composition of matter for reducing testosterone and/or DHT levels in a mammal in need of such treatment. Such a pharmaceutical composition of matter comprises at least one of the steroid compounds described above, mixtures thereof, and/or pharmaceutical salts thereof, and a pharmaceutically-acceptable carrier therefor. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa. (1985).

For therapeutic use in a method of inhibiting synthesis of testosterone and/or DHT, a steroid compound of the present invention, or its salt, can be conveniently administered in the form of a pharmaceutical composition containing a steroid compound according to the present invention, or its salt, and a pharmaceutically acceptable carrier therefor. Suitable carriers are well known in the art and vary with the desired form and mode of administration of the pharmaceutical composition. For example, they may include diluents or excipients such as fillers, binders, wetting agents, disintegrators, surface-active agents, lubricants, and the like. Typically, the carrier may be a solid, liquid, or vaporizable carrier, or combinations thereof. In one preferred embodiment, the composition is a therapeutic composition and the carrier is a pharmaceutically acceptable carrier.

The compound of the invention or its salt may be formulated together with the carrier into any desired unit dosage form. Typical unit dosage forms include tablets, pills, powders, solutions, suspensions, emulsions, granules, capsules, suppositories; injectable solutions and suspensions are particularly preferred.

Each carrier must be "acceptable" in the sense of being compatible with the other ingredients in the formulation and not injurious to the patient. The carrier must be biologically acceptable and inert, i.e., it must permit the cell to conduct its metabolic reactions so that the compound of this invention may effect its inhibitory activity.

Formulations include those suitable for oral, rectal, nasal, topical (including buccal and sublingual), vaginal and parenteral (including subcutaneous, intramuscular, intravenous, intradermal, and transdermal) administration, with formulations appropriate for oral, nasal, and parenteral administration being preferred.

For example, to prepare formulations suitable for parenteral administration, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such as sodium chloride, glucose or glycerin can be added to make the preparations isotonic. The aqueous sterile injection solutions may further contain antioxidants, buffers, bacteriostats, and like additions acceptable for parenteral formulations.

The formulations may conveniently be presented in unit dosage form and may be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation.

The compound of the invention may be present in the composition in an broad proportion to the carrier. For instance, the compound may be present in the amount of 0.01 to 99.9 wt %, and more preferably in about 0.1 to 99 wt %. Still more preferably, the compound may be present in an amount of about 1 to 70 wt % of the composition.

Also part of this invention is a method of treating BPH or prostate cancer, or inhibiting the growth of prostate tissue, in a patient in need of such treatment, by treating that patient with an effective amount of a steroid compound of the present invention, pharmaceutically acceptable salts thereof, or mixtures thereof. In this application, "treating" will encompass any means by which the compound of this invention contacts the cellular machinery responsible for synthesis of testosterone and/or DHT. Also, in this application "patient" will encompass any mammal in need of such treatment, particularly a mammal suffering from BPH or prostate cancer.

The dosage of the steroid compounds, pharmaceutically acceptable salts thereof, or mixtures thereof, in the compositions of the invention administered to a patient will vary depending on several factors, including, but not limited to, the age, weight, sex, and species of the patient, the general health of the patient, the severity of the symptoms, whether the composition is being administered alone or in combination with other therapeutic agents, the incidence of side effects and the like.

In general, a dose suitable for application in the treatment of BPH is about 0.001 to 100 mg/kg body weight/dose, preferably about 0.01 to 60 mg/kg body weight/dose, and still more preferably about 0.1 to 40 mg/kg body weight/dose per day. A dose suitable for application in the treatment of prostate cancer is about 0.001 to 100 mg/kg body weight/dose, preferably about 0.01 to 60 mg/kg body weight/dose, and still more preferably about 0.1 to 40 mg/kg body weight/dose per day. The desired dose may be administered as 1 to 6 or more subdoses administered at appropriate intervals throughout the day. The compounds may be administered repeatedly over a period of months or years, or it may be slowly and constantly infused to the patient. Higher and lower doses may also be administered.

The daily dose may be adjusted taking into account, for example, the above-identified variety of parameters. Typically, the present compositions may be administered in an amount of about 0.001 to 100 mg/kg body weight/day. However, other amounts may also be administered.

To achieve good plasma concentrations, the active compounds may be administered, for instance, by intravenous injection of an approximate 0.1 to 1% solution of the active ingredient, optionally in saline, or orally administered as a bolus.

The active ingredient may be administered for therapy by any suitable routes, including topical, oral, rectal, nasal, vaginal and parenteral (including intraperitoneal, subcutaneous, intramuscular, intravenous, intradermal, and transdermal) routes. It will be appreciated that the preferred route will vary with the condition and age of the patient, the nature of the disorder and the chosen active ingredient including other therapeutic agents. Preferred is the oral route. Also preferred is the topical route. However, other routes may also be utilized depending on the conditions of the patient and how long-lasting the treatment is.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients, including other steroid compounds and/or therapeutic agents in a pharmaceutical composition. Other therapeutic agents suitable for use herein are any compatible drugs that are effective by the same or other mechanisms for the intended purpose, or drugs that are complementary to those of the present agents. These include agents that are effective for the inhibition of testosterone and/or DHT synthesis, and in the treatment of prostate cancer, anticancer agents. Examples are ketoconazole, finasteride, and 4MA, among others.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

Having now generally described this invention, the same will be better understood by reference to certain specific examples, which are included herein for purposes of illustration only and are not intended to be limiting of the invention or any embodiment thereof, unless so specified.

EXAMPLE 1

Synthesis and evaluation of novel 20-pregnene and other steroid derivatives as inhibitors of testicular 17α-hydroxylase/$C_{17,20}$-lyase and prostatic 5α-reductase in vitro.

Over 70 20-substituted and other pregnene derivatives have been synthesized and evaluated as inhibitors of human 17α-hydroxylase/$C_{17,20}$-lyase and of 5α-reductase (Table 1 and 2).

The conversion of radiolabeled pregnenolone to 17α-hydroxypregnenolone and DHEA by 17α-hydroxylase/$C_{17,20}$-lyase was measured by incubating human testicular microsomes with different concentration of test compounds. Reverse phase HPLC was used to separate and accurately quantify the amount of substrate and metabolites. The 17α-hydroxylase and $C_{17,20}$-lyase activities were calculated separately. The activity of 17α-hydroxylase was calculated from the conversion of pregnenolone to 17α-hydroxypregnenolone and DHEA and the activity of $C_{17,20}$-lyase was based on the conversion of pregnenolone to DHEA. Although 17α-hydroxypregnenolone is the substrate converted to DHEA by $C_{17,20}$-lyase, it has been reported that this 17α-hydroxy intermediate is not released from the enzyme binding site during conversion (Nakajin et al., 1981a,b). Also, there are species differences in substrate requirements. Pregnenolone is the natural substrate rather than progesterone for human testicular 17α-hydroxylase and $C_{17,20}$-lyase. Therefore, pregnenolone was used as substrate for measuring the activity of this enzyme complex.

The 5α-reductase assay is performed by incubating human prostatic microsomes (approx. 0.6 mg protein in 0.5 ml phosphate buffer) with [7-$^3$H]testosterone (10 mM. 6×10$^5$ dpm) with a NADPH generating system (NADP 0.65 mM; glucose-6-phosphate 7.1 mM; glucose-6-phosphate dehydrogenase 2.5 IU in 100 μl phosphate buffer) and candidate inhibitors at concentrations of 10 nM and 100 nM under oxygen for 30 min at 37° C. Steroids [$^{14}$C]-labelled (T, A and DHT) and authentic markers (T, A, DHT, 5α-androstane-3α-diol and 3β-diol, the 3 diols) are added after the incubation. The steroids are extracted with ether and separated by chromatography on TLC (chloroform:ether 80:20). The DHT and 3-diols are located from their markers after exposure of the plate to iodine vapor. The steroids are scraped from the plate and radioactivity measured. Results are calculated from the percentage conversion of [7$^3$H] testosterone to DHT and the 3-diols.

As shown in Table 1, compounds containing 20-oxime (I-1, I-5), and 20β-ol (I-20, I-34) demonstrated potent inhibition of 17α-hydroxylase and of $C_{17,20}$-lyase. The 20β-carboxaldehyde (I-16; Li et al., 1992) and 20S-20,22-epoxide (I-8) exhibit significant inhibition of this enzyme complex. The 22-oxime (I-23) also showed potent inhibition of 5α-reductase and was the basis of U.S. Pat. No. 5,264,427, the contents of which are incorporated herein by reference. The 20-hydrazone (I-12) and 20-amine (I-9, I-10) showed poor inhibition, whereas the N,N dimethylhydrazones at 20-position (I-14) or 22-position (I-15) were devoid of inhibitory activity. This result implies that hydrophobic interactions between these substituents and the enzyme's active site are not favored. Similar effects can be seen in 20-ene (I-28) and 20-yne (I-29).

In modifying the D-ring, we found that the most important factor which contributes to the inhibition of this enzyme complex is the 16,17-ene when associated with 20-oxime (I-5). Thus, compared with the 20-oxime (I-1), the 16-en-20 oxime (I-5) showed 35-fold more potent inhibition. Other compounds, such as 16α,17α-epoxide (I-17) had decreased potency. The introduction of 17,20-ene did not contribute to inhibition (compare (I-26) to (I-32)), 17α-bromo (I-11) showed poor inhibition and 3-acetate (I-37) had less activity than the 3-hydroxy compound (I-36).

Introducing a 20-aza feature into the inhibitor I-16 as a bioisostere modification was expected to increase potency. However, 20-aza compound (I-40) showed approximately 4-fold lower inhibition than I-16.

The imidazole moiety has been introduced into inhibitors of several cytochrome P-450 enzymes, notably aromatase (Schieweck et al., 1993). The imidazole moiety may act as a ligand to bind to the iron atom of the heme prosthetic group of the cytochrome P-450 enzyme and form a coordinated complex. Although the detailed mechanism of the 17α-hydroxylation and $C_{17,20}$-side chain cleavage by 17α-hydroxylase/$C_{17,20}$-lyase is presently unclear, based on our inhibitor studies, it appears that the heme group of the enzyme must be close to the C17 and C20 positions of the substrate. Therefore, introduction of an imidazole group at these positions will place this group near to the heme. Using this rationale, we have designed and synthesized a series of pregnane derivatives with imidazole groups substituted at 17β- or 20-positions. This modification has turned out to be the most effective strategy for producing potent inhibitors. Compound I-47, containing 17β-(4'imidazolyl ring) demonstrated potent inhibition of 17α-hydroxylase/$C_{17,20}$-lyase (IC$_{50}$ 11/7 nM). This suggests that the imidazolyl nitrogen lone pair at this position could coordinate to the iron atom of the heme cofactor in the active site of the enzyme. The introduction of 16,17α-epoxide (I-51, IC$_{50}$ 431/98 nM) or 17α-hydroxy group (I-44, IC$_{50}$ 1,200/1000 nM) decreased this inhibition dramatically. However, the introduction of 16,17 double bond (I-49, IC$_{50}$ 4/4 nM) increased inhibition 2-fold. Potter et al. (1995) also found that 17-(3'-pyridyl) substituents together with a 16,17-double bond showed potent activity.

As to the modification of the imidazole ring, we found that the introduction of the methyl group at the 2' positions (L-4, IC$_{50}$ 400 nM) decreased this activity, while the large 2'-phenyl group caused almost total loss of activity. The 17β-(2'-imidazolyl) L-1) in which the steroid is bonded to the 2'-position of imidazole, showed poor inhibition of 17α-hydroxylase/$C_{17,20}$-lyase. The 20β-[4'-imidazolyl]-(I-45) also did not show any activity. These results suggested that the juxtaposition between the imidazole ring and the steroid D ring is important. 17β-[2'-methyl-4'oxazolyl] (L-5), the bioisostere analog of L-4 in which the N' atom is substituted by O atom, caused less inhibition. The 3-acetoxy derivative (L-12) had lower potency than I-49, which may reflect a limited bulk tolerance at the 3-position. However, L-12 still retained reasonable activity (IC$_{50}$ 75/25 nM) and might be useful as a prodrug of I-49 in vivo.

The above derivatives are based on the 5-ene-3β-ol structure and are similar to the natural substrate pregnenolone. However, the substrate for 5α-reductase is 4-ene-3-one, i.e., testosterone. As expected, I-47 and I-49 did not inhibit 5α-reductase. On the other had, I-41 and L-6, which are the 4-ene-3-one derivatives of I-47 and I-49, respectively, showed activity against 5α-reductase (IC$_{50}$=122 nM and 522 nM) while still retaining their strong potency against 17α-hydroxylase/$C_{17,20}$-lyase (IC$_{50}$, 59/5 nM and 16/2, respectively). Thus, to achieve total inhibition of androgen synthesis, I-41 and L-6 appear to be promising candidates.

The inhibitory activities of the 20-hydroxy epimers in 5-ene-3-ol, 4-ene-3-one, 5,16-diene-3-ol and 4,16-diene-3-one pregnane series were investigated. In the 5-pregnene-3-ol series, the 20β-ol (I-20) demonstrated stronger inhibition of 17α-hydroxylase/$C_{17,20}$-lyase (IC50m 180/190 nM) than the 20α-ol epimer (I-19, $IC_{50}$ 720/510 nM), although neither showed activity against 5α-reductase, as expected. The conversion from 5-ene-3-ol into 4-ene-3-one decreased inhibition of 17α-hydroxylase/$C_{17,20}$-lyase but greatly enhanced inhibition of 5α-reductase. Thus, 20α-ol (I-33) is a potent 5α-reductase inhibitor ($IC_{50}$ 13 nM) and is stronger than its 20β-ol-epimer (I-34, $IC_{50}$ 90 nM). As indicated above, the introduction of the 16,17-double bond increased inhibition of 17α-hydroxylase/$C_{17,20}$-lyase. Thus, L-8 (20α-hydroxy-5,16-pregnadiene-20-one) is stronger ($IC_{50}$=100 nM) than I-20, while 20β-ol )1–9) was less active. L-10, 20β-hydroxy-4,16 pregnadiene-3-ol is a potent 5α-reductase inhibitor ($IC_{50}$=20 nM) comparable to finasteride ($IC_{50}$=14 nM), while its epimer 20α-ol (L-11) showed no activity. As the 20β-ol of L-10 might be metabolized to 20-one in vivo, the 16-dehydroprogesterone (L-13) was also tested and found to be a potent inhibitor of both 17α-hydroxylase ($IC_{50}$=73/24 nM) and 5α-reductase ($IC_{50}$=22 nM). Progesterone is also known to be a potent 5α-reductase inhibitor, but its rapid metabolism in the body and lack of oral activity, detracts from its value as a therapeutic agent (Petrow et al, 1983). However, as L-10 and L-13 both have a 16,17-double bond, their 17β-acetyl side chain should be difficult to degrade in vivo.

As indicated, the introduction of 20-oxime group generally enhances inhibition of 17α-hydroxylase/$C_{17,20}$-lyase. Pregnenolon-20-oxime (I-5) is a more potent 17α-hydroxylase/$C_{17,20}$-lyase inhibitor ($IC_{50}$=16 nM/16 nM). The 4-ene-3-one derivative of I-5, L-2, not only showed twofold stronger activity against 17α-hydroxylase/$C_{17,20}$-lyase ($IC_{50}$=6/5 nM), but also showed potent activity for 5α-reductase ($IC_{50}$=52.5 nM). The introduction of the 3-oxime group (I-42, I-43) decreased activity against 17α-hydroxylase/$C_{17,20}$-lyase and 5α-reductase.

In summary, over 70 compounds have been synthesized and evaluated for enzyme inhibition. The most potent inhibitors are summarized in Table 3. I-47, I-49 and L-6 are potent inhibitors of 17α-hydroxylase/$C_{17,20}$-lyase and 5α-reductase. L-12 is a weaker inhibitor than I-49, but it might act as a prodrug of I-49 in vivo. We believe that some of our candidates are also very potent inhibitors of 17α-hydroxylase/$C_{17,20}$-lyase. The 17β-(cyclopropylamino)androst-5ene-3-ol was reported to have a $K_i$ of 90 nM. The 17β-ureido-substituted steroid with potent activity for the rat 17α-hydroxylase/lyase have been described (Goldman et al., 1976). Recently, Potter et al (1995) reported the most potent inhibitor, 17-(3'-pyridyl)androsta-5,16-diene-3-ol (CB7598) with an $IC_{50}$ of 4 nM/2.9 nM. However, this was tested against [$^3$H]-progesterone instead of the natural substrate [$^3$H]-pregnenolone. As the $IC_{50}$ of ketoconazole in their assay was 65 nM/26 nM, CB7598 had similar potency to L-2 and I-49. Most of our candidates, described above, are 10–50 times more active than ketoconazole. However, L-2, L-6, and L-13 also showed potent inhibition of 5α-reductase, whereas CB7598 showed no activity against this enzyme (Potter et al., 1995). The inhibitors presented here appear to have greater potential.

EXAMPLE 2

Inhibition of Adrenal Steroids

These studies were carried out using guinea pig adrenals. In contrast to the rat, the guinea pig synthesizes cortisol, like the human. Incubations have been carried out with many of the more potent testicular 17α-hydroxylase/$C_{17,20}$-lyase inhibitors to determine whether they also affect the adrenal 17α-hydroxylase/$C_{17,20}$-lyase required for cortisol production. A number of pregn-4-en-3-one derivatives appeared to inhibit the adrenal enzyme, whereas most pregn-5-en-3β-ol compounds had very little effect, e.g., I-47 and I-49. I-5 and I-7 were of interest, as they had relatively little (4%) or no effect on the adrenal 17α-hydroxylase required for cortisol synthesis but had moderately strong effects on the $C_{17,20}$-lyase causing reduction in adrenal androgen synthesis (77% and 63%, respectively).

EXAMPLE 3

The effect of inhibitors on androgen receptors.

Studies to determine whether the inhibitors interact with androgen receptors have been carried out with I-16, I-23, and I-47 to date. The ability of these compounds to antagonize the stimulatory effect of DHT on androgen receptor-mediated gene transcription was determined. In addition, the agonistic properties of the compounds were also investigated. CV1 cells were transiently transfected with a gene encoding either the human androgen receptor (AR) or a mutant AR which is expressed in LNCaP cells. Also transfected was a luciferase reporter vector under the control of the androgen response element of the mouse mammary tumor virus promoter. Treatments which activated the AR resulted in increased luciferase activity. This was quantified by lysing the cells, adding ATP and luciferin, and measuring the generated luminescence in a luminometer. In the absence of inhibitors, DHT (1 nM) stimulated luciferase activity 105–117-fold in cells transfected with wild-type AR. I-16, I-23, and I-47 all exhibited a dose-dependent antagonism of the wild-type receptor. In cells transfected with the mutant receptor of LNCaP cells, I-47 again behaved as an antagonist, whereas I-16 and I-23 acted as agonists.

EXAMPLE 4

The effect of inhibitors on androgen-dependent growth of the prostate in vitro.

Human Prostatic Cancer Cells (LNCaP)

The ability of various inhibitors to reverse the stimulatory effect of testosterone on the growth of the LNCaP human prostatic cancer cell line was tested by comparing cell number in wells treated for 9 days with either drug vehicle only (control), 0.1 nM testosterone only, or 0.1 nM testosterone with inhibitor at 0.3, 1, 2.5, or 5 μM. Testosterone stimulated the growth of LNCAP cells 2-fold compared to control cultures treated with drug vehicle only. I-47, I-49, L-10 and the reference compounds finasteride and 4-MA exhibited a dose-dependent reversal of the stimulatory effect of testosterone. I-23, I-33, I-34 and hydroxyflutamide (0.3–1 μM) stimulated cell proliferation. This effect is probably attributable to mutation of the androgen receptor of LNCaP cells which increases its responsiveness to progestins. The most effective compounds were I-47, 4MA and finasteride, which all reduced the stimulatory effect of 0.1 nM testosterone by 50% at a concentration of 1 μM or lower and almost completely reversed the effect of testosterone at 5 μM. The cells were also incubated with 0.03 nM DHT which stimulated the growth of LNCaP cells by 2.8-fold. I-47, I49, 4-MA and finasteride all produced a dose-dependent reversal of the stimulatory effect of DHT, with I-47 and I-49 producing nearly complete reversal at 5 μM. The inhibitory effect of L-10 was not dose-dependent over the concentration range tested. Inhibitors I-23 and I-34 produced stimulation of growth above the level produced by DHT.

Prostate Tissue in Histoculture

We recently developed a histoculture method to evaluate the growth inhibiting properties of the compounds on human prostatic tissue. Surgical biopsies of human BPH or prostate cancer tissue from patients were cut into small pieces and incubated on gelatin sponges in 1 ml Eagle's MEM (without phenol red) with 5% charcoal-stripped fetal bovine serum and testosterone or DHT substrate with/without inhibitors in 24-well plates for 7 days at 37° C. The tissue samples were then incubated for 3 days in fresh medium/treatment containing 2 $\mu$Ci/ml [$^3$H]-thymidine. Tissue was then digested and DNA extracted. For each sample, [$^3$H]-thymidine uptake was normalized to DNA content. Testosterone (1 $\mu$M) and DHT (10 nM) stimulated DNA synthesis approximately 2-fold and 3-fold, respectively, in comparison to untreated samples. I-33, I-34, I-47, 4MA and flutamide (1 $\mu$M) produced almost complete reversal of the stimulatory effect of testosterone (FIG. 1), whereas I-49 was partially effective, and I-41 and I-43 were without effect (data not shown). I-33 and 4-MA were also highly effective at 0.3 $\mu$M, whereas I-34 was partially effective suggesting that inhibition of 5$\alpha$-reductase by these compounds was sufficient to inhibit growth. The stimulatory effect of DHT was almost completely reversed by 1 $\mu$M I-47. This finding is consistent with the compound acting as an antiandrogen. None of the compounds produced an independent effect on DNA synthesis in the absence of added androgens.

Conclusions

The results to date show that compounds I-47, I-49, L-2, L-6 and L-13 are 10–50 times more potent than ketoconazole for the human 17$\alpha$-hydroxylase/C$_{17,20}$-lyase. Furthermore, L-2 is also a potent inhibitor of human 5$\alpha$-reductase and only slightly less potent (4–6 times) than finasteride, whereas L-10 and L-13 are almost equipotent with finasteride. Data to date indicate that L-2 and L-13 are the best compounds as they are potent inhibitors of both enzymes. The ability of I-33 and 4MA to inhibit testosterone stimulation of DNA synthesis in histocultures of prostate tissue could be at least partially attributed to their inhibitory effects on 5$\alpha$-reductase. Compound I-47, however, has no activity against 5$\alpha$-reductase, and yet was able to inhibit the growth-stimulatory effect of not only testosterone, but also DHT, both in histoculture of prostatic tissue and in cell cultures of the LNCAP cell line. This suggests that I-47 act as an antagonist of the androgen receptor as well as a potent inhibitor of 17$\alpha$-hydroxylase/C$_{17,20}$-lyase. Transcriptional assays confirmed this hypothesis. Unlike hydroxyflutamide, which has been found to have agonist activity for the mutant androgen receptor of LNCaP cells (Veldscholte et al., 1992), I-47 is not an agonist of the mutant receptor. Thus, I-47 may have an advantage over the currently used antiandrogen, hydroxyflutamide for the treatment of prostatic cancer, since the LNCAP mutation has been found frequently in the androgen receptors of prostate tumor biopsies (Gaddipati et al., 1994). The dual antiandrogenic-17$\alpha$-hydroxylase/C$_{17,20}$-lyase inhibitory effects of I-47 increases its potential utility in the treatment of prostatic cancer.

EXAMPLE 5

In vivo studies in normal rats.

Studies in normal male rats have been carried out with 4-pregnen-3-one-20$\beta$-carboxaldehyde (I-16) (Li et al., 1992) and with its 20-carboxaldoxime (I-23)(Li et al., 1995). Both compounds inhibit rat 17$\alpha$-hydroxylase/C$_{17,20}$-lyase as well as 5$\alpha$-reductase and were effective in significantly reducing testosterone and DHT levels in serum, testicular and prostatic tissues in the rat. The 3-oxo-4-pregnene-20$\beta$-carboxaldehyde oxime (I-23) demonstrated moderate inhibition of the 17$\alpha$-hydroxylase (K$_i$ 74 nM vs K$_m$ 29 nM) with progesterone as substrate and potent inhibition (K$_i$ 18 nM vs. K$_m$ 76 nM) of the C$_{17,20}$-lyase activity with 17$\alpha$-hydroxyprogesterone as substrate. Further investigation of this enzyme with progesterone as substrate demonstrated that inhibition occurred mainly at the 17$\alpha$-hydroxylation step. I-23 also demonstrated potent and competitive inhibition of 5$\alpha$-reductase in human prostatic microsomes (K$_i$ 1.4 nM vs. K$_m$ 14 nM). When adult male rats were injected sc daily with I-23 (50 mg/kg/day) for 21 days, the concentrations of serum and testicular testosterone were significantly reduced by 65% and 59%, respectively, in comparison to vehicle treated controls. Furthermore, both testosterone and DHT concentrations in rat prostatic tissue were significantly decreased by 60% and 44% compared to control tissue. Serum LH concentrations were unchanged in the I-23 treated group compared to the control group. This indicates that the reduction in androgen concentrations in animals treated with this compound is not due to its influence on pituitary feedback mechanisms which result in reduced LH secretion. These findings suggest that I-23 is effective in reducing androgen synthesis through the inhibition of 17$\alpha$-hydroxylase/C$_{17,20}$-lyase and 5$\alpha$-reductase both in vitro and in vivo (Li et al., 1995).

EXAMPLE 6

Studies in human prostatic cancer xenografts model.

We have reported that inoculation of MCF-7 breast cancer cells in Matrigel increases mammary tumor formation in nude mice (Yue et al., 1994). The same procedure was therefore utilized to develop tumors from human prostatic cancer cells (LNCAP) in male nude mice. BALB/c male athymic mice, 4–6 weeks old, were inoculated sc with LNCaP cells suspended in Matrigel (10 mg/ml). Four sites per mouse were injected with $1.8\times10^6$ cells in 0.1 ml Matrigel. Treatment began when the tumor reached about 100 mm$^3$ in volume. Tumors were measured before the treatment began and once a week during treatment. Tumor volume was calculated by the formula $4/3\pi r_1^2 r_2$ ($r_1 < r_2$). At the end of treatment, the mice were sacrificed and individual tumors were weighed. The latency of tumor development was 30–40 days and overall tumorigenicity was 82%.

Figure 2:
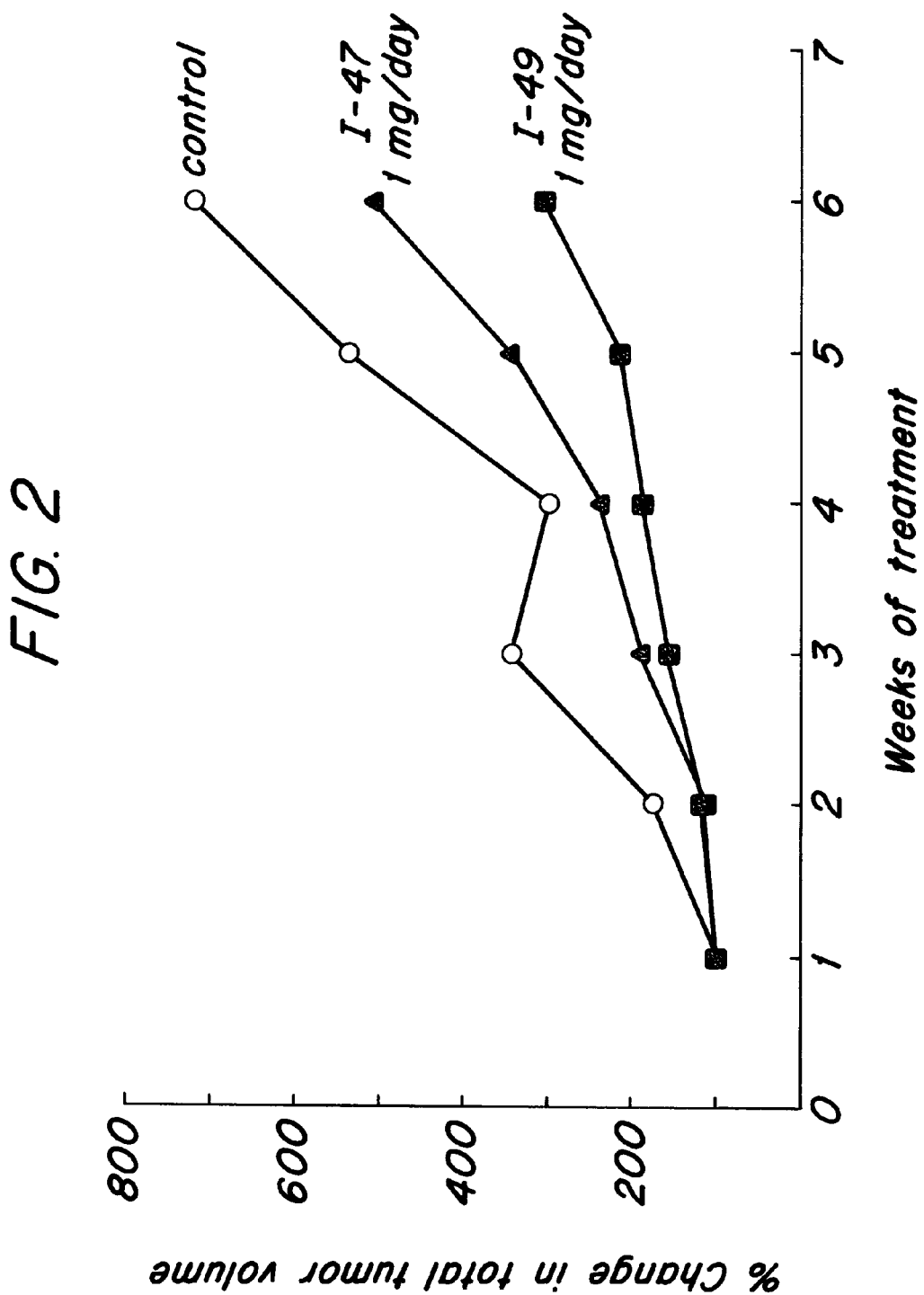
FIG. 2 illustrates the effect of androgen synthesis inhibitors of the present invention on volume of human prostatic tumors in a nude mouse model.

In a further experiment, two mice were treated with I-16 (1 mg/mouse/day, s.c.) beginning 45 days after cell inoculation. Two mice received vehicle as controls. After 3 weeks of treatment, the total tumor volume of the control mice had increased to 281% of their initial volume, whereas in I-6 treated mice the total tumor volume was 173.6%. The mean tumor weight was 198.78±72 mg in I-16 treated mice compared to 386.3±147.2 mg in the control group. In other experiments, I-47 and I-49 were effective in controlling tumor growth. The total tumor volume of the control mice increased to 884.0% of the initial volume. In five weeks, the tumor growth rate of 4 mice per group was reduced by treatment with I-47 and I-49 (525.8% and 315.3% of their initial volumes, respectively (FIG. 2)). The mean tumor weight was 1310.5±1125.9 mg in the control mice, 607.0±142.4 mg in the I-47 treated group and 255.9±176.9 mg (p<0.05 compared to the control) in the I-49 treated group.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

TABLE 1

Inhibition of Human Testicular 17α-Hydroxylase/$C_{17,20}$-lyase by Steroid Derivatives

| Basic Structure # | Substituents | % Inhibition [I] = 100 nM | % Inhibition [I] = 400 nM | $IC_{50}$ (μM) 17α-OHase | $IC_{50}$ (μM) $C_{17,20}$lyase |
|---|---|---|---|---|---|
| Pregn-5-en-3β-ol | | | | | |
| I-1 | 20-one oxime | | | 0.53 | 0.57 |
| I-5* | 16-en-20-one oxime | | | 0.016 | 0.016 |
| I-7 | (20R)-20,22-epoxide | | | 0.72 | 0.72 |
| I-8 | (20S)-20,22-epoxide | | | 0.11 | 0.14 |
| I-11* | 17α-bromo-20-one | | | 1.30 | 0.97 |
| I-9 | 20β-amine | | | 89.8 | 43.9 |
| I-10 | 20α-amine | | | 9.8 | 8.0 |
| I-12 | 20-one hydrazone | | | 9.98 | 4.90 |
| I-13 | 20-one N,N-dimethyl-hydrazone | | | NI | NI |
| I-14 | 16-en-20-one N,N-dimethylhydrazone | | | 43.7 | 35.0 |
| I-17* | 16α,17α-epoxy-20-one | | | 0.44 | 0.68 |
| I-19* | 20α-ol | | | 0.72 | 0.51 |
| I-20* | 20β-ol | | | 0.18 | 0.19 |
| I-28 | 20-ene | | | 2.88 | 3.71 |
| I-29 | 20-yne | | | 3.56 | 3.95 |
| I-31 | 20β-carboxyaldehyde | | | 0.08 | 0.08 |
| I-36* | 16-en-20-one | | | 0.51 | 0.49 |
| I-37* | 16-en-20-one 3-acetate | | | 1.89 | 1.71 |
| L-8 | 20β-hydroxy-16-ene | 53.97/66.18 | 82.71/83.32 | | |
| L-9 | 20α-hydroxy-16-ene | NT | NT | | |
| L-18 | 20,20β-aziridinyl- | 21.81/42.95 | 56.12/81.09 | | |
| L-21 | 17α,30α-azirdinyl- | 8.47/29.15 | 23.73/52.04 | | |
| L-22 | 17β,20β0aziridinyl- | 0.0/3.33 | 0.0/9.99 | | |
| Pregn-4-3n-3-one | | | | | |
| I-15 | 20β-carboxaldehyde N,N-dimethylhydrazone | | | NI | NI |
| I-16* | 20β-carboxaldehyde | | | 0.23 | 0.16 |
| I-18* | 16α,17α-epoxy-20-one | | | 0.48 | 0.80 |
| I-23 | 20β-carboxaldoxime | | | 5.98 | 6.97 |
| I-26 | 17(20)-en-20-cyano | | | 1.22 | 0.89 |
| I-32 | 20β-cyano | | | 1.10 | 0.75 |
| I-33* | 20α-ol | | | 2.84 | 1.43 |
| I-34* | 20β-ol | | | 0.49 | 0.24 |
| I-35 | 16-en-20-one | | | 1.77 | 1.70 |
| I-42 | 3(Z),20-dioxime | | | 0.21 | 0.22 |
| I-43 | 3(E),20-dioxime | | | 0.09 | 0.07 |
| I-45 | 20β-[4'-imidazolyl]- | | | >30 | >30 |
| L-2 | 20-oxime | | | 0.0087 | CI |
| L-13 | 20-one | | | 0.073 | 0.024 |
| L-10 | 20β-hydroxy | 14.90/2.28 | 8.19/8.48 | | |
| L-11 | 20α-hydroxy | NI | | | |
| Androst-5-ene-3β-ol | | | | | |
| I-2* | 17-one oxime | | | 13.5 | 10.7 |
| I-3* | 17-one hydrazone | | | 6.48 | 3.78 |
| I-39 | N-methyl-17β-formamide | | | 0.29 | 0.28 |
| I-47 | 17β-imidazole | | | 0.025 | 0.023 |
| I-49 | 16-en-17β-imidazole | | | 0.008 | 0.009 |
| I-51 | 17,17α-epoxy-17β-[4'-imidazolyl]- | | | 0.43 | 0.10 |
| I-53 | 16-ene-17-carboxylic ethyl ester | | | 3.04 | 2.45 |
| I-56 | 17-one N,N-dimethylhydrazone | | | 4.20 | 2.40 |
| L-1 | 17β-[2'imidazolyl]- | 22.84/73.89 | 23.69/100 | | |
| L-4 | 17β-[5'-methyl-4-imidazolyl] | 13.83/70.16 | 41.88/100 | | |
| L-5 | 17β-[2'-methyl-4'-imidazolyl] | 22.42/71.23 | 26.48/81.71 | | |
| L-7 | 17β-[5'-phenyl-4'-imidazolyl] | 10.30/9.50 | 20.93/33.83 | | |
| L-12 | 16-ene-17-[4'-imidazolyl]-3β-o-acetate | 62.36/82.06 | 89.31/97.03 | 0.075 | 0.025 |

TABLE 1-continued

Inhibition of Human Testicular 17α-Hydroxylase/$C_{17,20}$-lyase by Steroid Derivatives

| Basic Structure # | Substituents | % Inhibition [I] = 100 nM | % Inhibition [I] = 400 nM | IC$_{50}$ (μM) 17α-OHase | IC$_{50}$ (μM) $C_{17,20}$lyase |
|---|---|---|---|---|---|
| Androst-4-en-3-one | | | | | |
| I-4* | 17α-ethynyl-17β-ol | | | NI | NI |
| I-40 | N-methyl-17β-formamide | | | 0.76 | 0.68 |
| I-41 | 17β-[4'-imidazolyl]- | | | 0.059 | 0.005 |
| I-44 | 17α-hydroxy-17β-[4'-imidazolyl] | | | 1.2 | 1.00 |
| L-3 | 17β-[2'-imidazolyl] | 20.33/62.88 | 43.52/100 | | |
| L-6 | 16-ene-17β-4'-imidazolyl] | | | 0.016 | CI |
| L-15 | 5,19β-cycloandrost-1-ene-3,17-dione | 7.25/28.78 | NT | | |
| Ketoconazole | | | | 0.44 | 0.15 |

IC$_{50}$ refers to the inhibitor concentration which produced 50% inhibition of the enzyme activity.
NI = no inhibition; CI = complete inhibition; NT = not tested.

TABLE 2

Inhibition of Human Prostatic 5α-Reductase by Steroid Derivatives

| Base Structure Compound # | Substituents | % Inhibition [I] 10 nM | 100 nM | 400 nM | IC$_{50}$ (μM) |
|---|---|---|---|---|---|
| Pregn-5-en-3β-ol | | | | | |
| I-5* | 16-en-20-one oxime | 0 | 5.92 | | |
| I-7 | (20R)-20,22-epoxide | 13.64 | 12.08 | | |
| I-8 | (20S)-20,22-epoxide | 11.85 | 16.26 | | |
| L-8 | 20β-hydroxy-16-ene | 37.13 | | | |
| L-9 | 20α-hydroxy-16-ene | 33.22 | | | |
| Pregn-4-3n-3-one | | | | | |
| I-15 | 20β-carboxaldehyde N,N-dimethylhydrazone | 16.41 | 74.93 | | |
| I-16* | 20β-carboxaldehyde | 20.54 | 87.15 | | |
| I-18* | 16α,17α-epoxy-20-one | 15.10 | 76.16 | | |
| I-23 | 20β-carboxaldoxime | 14.66 | 85.82 | | 0.106 |
| I-26 | 17(20)-en-20-cyano | 5.21 | 71.76 | | |
| I-32 | 20β-cyano | 20.98 | 79.15 | | |
| I-33* | 20α-ol | 28.51 | 87.59 | | 0.013 |
| I-34* | 20β-ol | 16.13 | 64.54 | | 0.09 |
| I-40 | N-methyl-17β-formamide | | | | 0.15 |
| I-41 | 17β-[4'-imidazolyl] | | | | NT |
| L-13 | 16-ene-20-one | | 87.77 | 96.39 | 0.022 |
| L-2 | 16-ene-20-oxime | | 45.47 | | 0.052 |
| L-10 | 16-ene-20β-hydroxy | 96.97 | 90.7 | | 0.021 |
| L-11 | 16-ene-20α-hydroxy | | | | NI |
| Androst-4-en-3-one | | | | | |
| I-42 | 3(E),20-dioxime | | | | 2.06 |
| I-43 | 3(Z),20-dioxime | | | | 1.27 |
| L-3 | 17β-[2'-imidazolyl] | | 31.70 | 61.69 | |
| L-6 | 16-ene-17β-[4'-imidazolyl] | | 25.22 | | 0.522 |
| L-15 | 5,19β-cycloandrost-1-ene-3,17-dione | | 23.31 | 60.93 | |
| L-14 | 17β-Acetoxy-6-methylene-5α-androst-3-one | | 5.77 | 11.39 | |
| L-19 | 17β,19(S)-dihydroxy 5,19β-cycloandrost-3-one | | 8.70 | 14.77 | |
| L-20 | 19(R)-Hydroxy-5,19β-cyclo-androst-3,17-dione | | 5.89 | 12.24 | |
| L-23 | 4α-methyl-19-(S)-methoxy-5,19β-cycloandrost-3,17-dione | | 0.0 | 16.06 | |
| L-24 | 19-Bromo-androst-4-ene-3,17-dione | | 12.35 | 52.72 | |
| Androst-5-ene-3β-ol | | | | | |
| I-49 | 16-ene-17β-[4'-imidazolyl] | | 26.27 | | |
| I-47 | 17β-[4'-imidazolyl] | | NT | | |
| | Finasteride | 41.19 | 88.28 | 93.01 | 0.014 |
| | 4MA | 71.91 | 92.01 | | 0.01 |

NI = no inhibition; NT = not tested.

TABLE 3

Summary of the Most Potent Inhibitors

| Basic Structure | | IC$_{50}$ (nM) | |
|---|---|---|---|
| Compound # | Substituents | 17α-hydroxylase/lyase | 5α-reductase |
| Androst-5-ene-3-ol | | | |
| I-47 | 17β-[4'-imidazolyl]- | 25.18 / 22.61 | NI |
| I-49 | 16-ene-17-[4'-imidazolyl]- | 8.82 / 9/48 | NI |
| L-12 | 3-acetoxy-16-ene-17β-[4'-imidazolyl]- | 74.63 / 24.85 | NT |
| Androst-4-ene-3-one | | | |
| L-41 | 17β-[4'imidazolyl]- | 59.35 / 5.61 | 122.0 |
| L-6 | 16-ene-17-[4'-imidazolyl]- | 15.63 / CI | 522.0 |
| Pregn-4,16-diene-3-one | | | |
| L-2 | 20-oxime | 8.65 / CI | 52.49 |
| L-10 | 20β-hydroxy- | NI | 21 |
| L-13 | 20-one | 72.68 / 23.74 | 21.79 |
| Known compounds | | | |
| | finasteride | NI | 14.4 |
| | ketoconazole | 437 / 150 | NI |

NI = No Inhibition; CI = Complete Inhibition; NT = Not Tested

What is claimed is:

1. A compound of the formula:

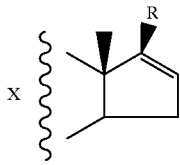

wherein X represents the residue of the A, B, and C rings of a steroid such that the compound has a 4-en-3-one structure, and R is selected from the group consisting of

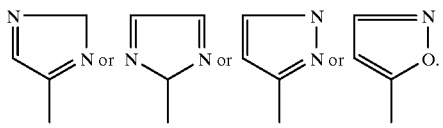

2. A compound according to claim 1, wherein the compound is 17β-(4'-imidazolyl)-androsta-4,16-dien-3-one.

3. A compound according to claim 1, wherein the compound is 17β-(3'-pyrazolyl)-androsta-4,16-dien-3-one.

4. A compound according to claim 1, wherein the compound is 17β-(5'-isoxazolyl)-androsta-4,16-dien-3-one.

5. A pharmaceutical composition comprising at least one compound according to claim 1 and a pharmaceutically acceptable carrier therefor.

6. A method of reducing plasma testosterone and DHT levels in an animal in need of such treatment comprising administering to said animal in an amount sufficient to reduce plasma testosterone and DHT levels at least one compound of the formula:

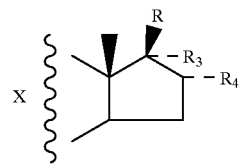

where X represents the residue of the A, B, and C rings of a steroid; R represents a 5-member heterocyclic ring, and $R_3$ and $R_4$ represent a hydrogen atom or together represents a double bond.

7. The method according to claim 6, wherein $R_3$ and $R_4$ together represent a double bond.

8. The method according to claim 6, wherein R is selected from the group consisting of

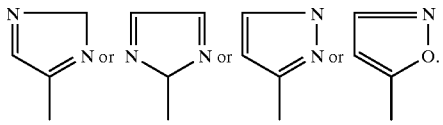

9. The method according to claim 6, wherein said compound has a 4-en-3-one, 5-en-3β-ol or 3,5-diene-3-carboxylic acid structure.

10. The method according to claim 6, wherein the compound is selected from the group consisting of 17β-(4'-imidazolyl)-androst-5-en-3β-ol, 17β-(4'-imidazolyl)-androsta-5,16-dien-3β-ol, 17β-(2'-imidazolyl)-androst-5,16-dien-3β-ol, 17β-(3'-pyrazolyl)-androst-5-en-3β-ol, 17β-(3'-pyrazolyl)-androsta-5,16-dien-3β-ol, 17β-(5'-isoxazolyl)-androsta-5,16-dien-3β-ol, and 3-acetates thereof.

11. The method according to claim 6, wherein the compound is selected from the group consisting of 17β-(4'-imidazolyl)-androst-4-en-3-one, 17β-(4'-imidazolyl)-androsta-4,16-dien-3-one, 17β-(3'-pyrazolyl)-androst-4-en-3-one, 17β-(3'-pyrazolyl)-androsta-4,16-dien-3-one, and 17β-(5'-isoxazolyl)-androsta-4,16-dien-3-one.

12. A method of treating benign prostatic hypertrophy in an animal in need of such treatment comprising administering to said animal in an amount sufficient to reduce the size of the prostate gland at least one compound of the formula:

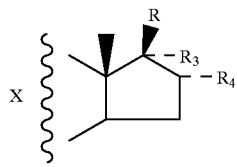

where X represents the residue of the A, B, and C rings of a steroid; R represents a 5-member heterocyclic ring, and $R_3$ and $R_4$ represent a hydrogen atom or together represents a double bond.

13. The method according to claim 12, wherein $R_3$ and $R_4$ together represent a double bond.

14. The method according to claim 12, wherein R is selected from the group consisting of

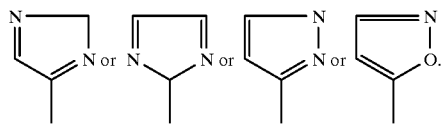

15. The method according to claim 12, wherein said compound has a 4-en-3-one, 5-en-3β-ol or 3,5-diene-3-carboxylic acid structure.

16. The method according to claim 12, wherein the compound is selected from the group consisting of 17β-(4'-imidazolyl)-androst-5-en-3β-ol, 17β-(4'-imidazolyl)-androsta-5,16-dien-3β-ol, 17β-(2'-imidazolyl)-androst-5,16-dien-3β-ol, 17β-(3'-pyrazolyl)-androst-5-en-3β-ol, 17β-(3'-pyrazolyl)-androsta-5,16-dien-3β-ol, 17β-(5'-isoxazolyl)-androsta-5,16-dien-3β-ol, and 3-acetates thereof.

17. The method according to claim 12, wherein the compound is selected from the group consisting of 17β-(4'-imidazolyl)-androst-4-en-3-one, 17β-(4'-imidazolyl)-androsta-4,16-dien-3-one, 17β-(3'-pyrazolyl)-androst-4-en-3-one, 17β-(3'-pyrazolyl)-androsta-4,16-dien-3-one, and 17β-(5'-isoxazolyl)-androsta-4,16-dien-3-one.

18. A method of treating prostate cancer in an animal in need of such treatment comprising administering to said animal in an amount sufficient to reduce the size of prostate tumors at least one compound of the formula:

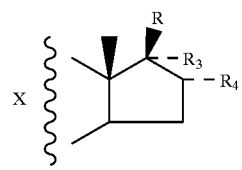

where X represents the residue of the A, B, and C rings of a steroid; R represents a 5-member heterocyclic ring, and $R_3$ and $R_4$ represent a hydrogen atom or together represents a double bond.

19. The method according to claim 18, wherein $R_3$ and $R_4$ together represent a double bond.

20. The method according to claim 18, wherein R is selected from the group consisting of

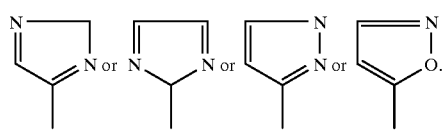

21. The method according to claim 18, wherein said compound has a 4-en-3-one, 5-en-3β-ol or 3,5-diene-3-carboxylic acid structure.

22. The method according to claim 18, wherein the compound is selected from the group consisting of 17β-(4'-imidazolyl)-androst-5-en-3β-ol, 17β-(4'-imidazolyl)-androsta-5,16-dien-3β-ol, 17β-(2'-imidazolyl)-androst-5,16-dien-3β-ol, 17β-(3'-pyrazolyl)-androst-5-en-3β-ol, 17β-(3'-pyrazolyl)-androsta-5,16-dien-3β-ol, 17β-(5'-isoxazolyl)-androsta-5,16-dien-3β-ol, and 3-acetates thereof.

23. The method according to claim 18, wherein the compound is selected from the group consisting of 17β-(4'-imidazolyl)-androst-4-en-3-one, 17β-(4'-imidazolyl)-androsta-4,16-dien-3-one, 17β-(3'-pyrazolyl)-androst-4-en-3-one, 17β-(3'-pyrazolyl)-androsta-4,16-dien-3-one, and 17β-(5'-isoxazolyl)-androsta-4,16-dien-3-one.

* * * * *

UNITED STATES PATENT AND TRADEMARK OFFICE
CERTIFICATE OF CORRECTION

PATENT NO.   : 5,994,334
DATED        : November 30, 1999
INVENTOR(S)  : Brodie et al.

It is certified that error appears in the above-identified patent and that said Letters Patent is hereby corrected as shown below:

Column 1,
Line 5, the following information should be included:

-- U.S. Government Support
     This work was supported in part by a grant from NIH (CA27440). --

Signed and Sealed this

Sixth Day of November, 2001

Attest:

NICHOLAS P. GODICI
Attesting Officer    Acting Director of the United States Patent and Trademark Office